United States Patent [19]

Chance et al.

[11] 3,937,724

[45] Feb. 10, 1976

[54] ORGANO-PHOSPHORUS COMPOUNDS CONTAINING PERFLUOROALKYL RADICALS AND THEIR APPLICATION TO CELLULOSIC TEXTILES

[75] Inventors: Leon H. Chance; Jerry P. Moreau, both of New Orleans, La.

[73] Assignee: The United States of America as represented by the Secretary of Agriculture, Washington, D.C.

[22] Filed: Mar. 24, 1975

[21] Appl. No.: 561,587

Related U.S. Application Data

[62] Division of Ser. No. 151,507, June 9, 1971, which is a division of Ser. No. 843,200, July 18, 1969, Pat. No. 3,639,144.

[52] U.S. Cl. .......................................... 260/502.4 P
[51] Int. Cl.$^2$ .......................................... C07F 9/38
[58] Field of Search ............................. 260/502.4 P

[56] References Cited
UNITED STATES PATENTS

| | | | |
|---|---|---|---|
| 3,297,578 | 1/1967 | Crutchfield et al. | 260/502.4 P |
| 3,419,595 | 12/1968 | Hansen | 260/502.4 P |
| 3,493,639 | 2/1970 | Tars | 260/502.4 P |
| 3,636,088 | 1/1972 | Chance et al. | 260/502.4 R |
| 3,701,817 | 10/1972 | Maier | 260/502.4 P |

*Primary Examiner*—Joseph E. Evans
*Attorney, Agent, or Firm*—M. Howard Silverstein; Max D. Hensley

[57] ABSTRACT

Perfluoroalkyl iodide monomer and telomer ester adducts of diethyl vinylphosphonate were prepared by free radical addition. Iodine of these adducts was replaced by hydrogen, and derivatives of the reduced phosphonate adducts were prepared, which include phosphonic acids, acid chlorides, and aziridinyl phosphine oxides. The aziridinyl phosphine oxides are used to impart oil and water repellency to cellulosic textiles. The other derivatives are useful as chemical intermediates as well as potential foaming agents.

1 Claim, No Drawings

ORGANO-PHOSPHORUS COMPOUNDS CONTAINING PERFLUOROALKYL RADICALS AND THEIR APPLICATION TO CELLULOSIC TEXTILES

This is a division of application Ser. No. 151,507, filed June 9, 1971, which in turn is a division of Ser. No. 843,200, filed July 18, 1969, now U.S. Pat. No. 3,639,144.

This invention relates to perfluoroalkyl adducts of diethyl vinylphosphonate, to derivatives thereof, to the preparation thereof, and to processes for imparting improved properties to cellulosic textiles by treating said textiles with certain of the perfluoroalkyl phosphorus derivatives of this invention. More specifically, this invention relates to the preparation of perfluoroalkyl phosphonate esters and to the corresponding acids, acid chlorides, and aziridinyl derivatives, useful in oil and water repellent finishes for textiles and also useful as chemical intermediates and potential foaming agents.

DEFINITIONS

1. "Telomers are polymers of low molecular weight such as are encountered, for example, in the free-radical addition of an addendum XY to ethylene, which may be represented as $XY + {}_nCH_2{:}CH_2 \rightarrow X(CH_2CH_2)_n Y$ where $n$ is small; the process is known as telomerization." Kingzett's Chemical Encyclopaedia, 9th Ed.

2. "Telomerization does not differ essentially from other polymerization catalyzed by free radicals. It arises merely because enough of a sufficiently reactive compound is present to act as a chain transfer reagent, but the concentration and reactivity are not high enough to give rise chiefly to 1,2, addition." Carl R. Noller's "Chemistry of Organic Compounds."

The main object of the instant invention is to disclose new phosphonic compounds containing a perfluoroalkyl radical connected to the phosphorus atom by an ethylene ($-CH_2CH_2-$) linkage.

A second object of the instant invention is to provide methods of preparing new perfluoroalkyl phosphonic compounds.

A third object of the instant invention is to provide a process for imparting to cotton and other cellulosic materials both oil and water repellency using some of the new compounds of the instant invention.

A fourth object of the invention is to provide a process for imparting to cotton and other cellulosic textiles resistance to soiling and staining.

Searching the prior art we find that a dialkyl phosphonate reacts with tetrafluoroethylene in a pressure vessel using a free radical initiator to produce products of the general formula $H(CF_2CH_2)_n PO(OR)_2$. [Neal D. Brace, J. Org. Chem. 26, 3197 (1961).] These products have a terminal hydrogen atom on the perfluoro group, and consequently are not as effective in producing oil and water repellency as similar products in which the terminal hydrogen is replaced by a fluorine atom.

One improvement which is a facet of the present invention over the prior art is this. We have found that compounds of the present invention impart excellent oil repellency and moderate water repellency to cellulosic materials because the perfluoro grpup has a terminal $CF_3$ group instead of a terminal $HCF_2$ group.

In the course of investigation we have found that compounds of the general formula

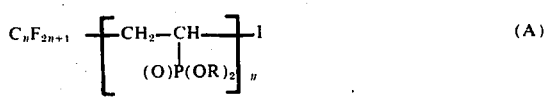

where $n$ is an integer from 1 to 10, R is an alkyl radical, and $y$ is an interger from 1 to 3 can be prepared by reacting a perfluoroalkyl iodide with a dialkyl vinylphosphonate in the presence of a free radical catalyst.

We have also found that a series of reactions can be carried out beginning with compounds represented by graphic formula (A) to produce products represented by the following equations:

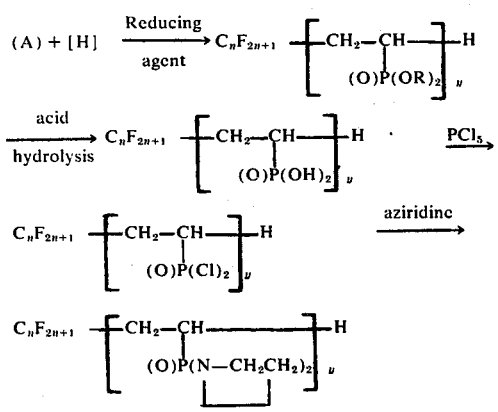

where $n$ is an integer from 1 to 10, and $y$ is an integer from 1 to 3.

In accordance with the present invention the reaction of the dialkyl vinylphosphonate with the perfluoroalkyl iodide is carried out by heating in the presence of a select catalyst. Typical catalysts suitable for the reaction are organic peroxides, such as di- tert- butyl peroxide or azobisnitriles such as azobis(isobutyronitrile). Two main products are obtained from this type reaction and include the monomeric perfluoroalkyl iodide adduct and a telomer in which the dialkyl phosphonate moiety is dimeric. A mixture of unidentified higher molecular weight telomers are also obtained. Typical examples are represented by the reaction of diethyl vinylphosphonate and perfluoroheptyl iodide to give a monomeric phosphonate ester of the formula $C_7F_{15}CH_2CH(I)P(O)(OC_2H_5)_2$ and a telomer ester of the formula

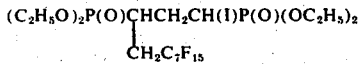

Also in accordance with the present invention the iodine atom is removed from the perfluoroalkyl phosphonate esters by a reducing agent, and replaced by a hydrogen atom. The preferred reducing agent is zinc metal and hydrochloric acid. Typical reduced phosphonate esters are represented by a monomer of the formula $C_7F_{15}CH_2CH_2P(O)(OC_2H_5)_2$ and a telomer of the formula

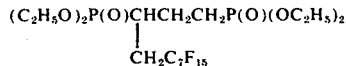

The conversion of the reduced phosphonate esters to the phosphonic acids is carried out by hydrolysis in the presence of a mineral acid. The preferred acid is hydrochloric acid. The conversion of the phosphonic acids to the phosphonic dichloride is carried out by heating with $PCl_5$ in a suitable solvent. The preferred solvent is carbon tetrachloride.

The conversion of the phosphonic dichloride to the diaziridinyl derivative is carried out by reaction with aziridine in a suitable organic solvent in the presence of an acid acceptor. A variety of solvents are suitable and include benzene and chlorinated solvents such as carbon tetrachloride or methylene chloride. Suitable acid acceptors include tertiary organic bases such as triethylamine and inorganic bases such as sodium or potassium hydroxide. The preferred base is triethylamine. Typical diaziridinyl derivatives are represented by a monomer of the formula

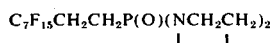

and a telomer of the formula

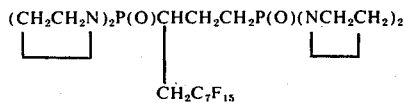

Each of the new type perfluoroalkyl phosphonic compounds mentioned above is useful as a precursor to the type compound which follows. Finally, the aziridinyl derivatives are useful as oil and water repellents for textiles, particularly for cotton or other cellulosic textiles, and for paper. The phosphonic acid derivatives have use as potential foaming agents.

The perfluoroalkyl aziridinyl phosphine oxide can be applied to cellulosic materials from a variety of solvents. Suitable solvents are water, alcohols such as ethanol or methanol and glycol ethers such as ethylene glycol monoethyl ether. The preferred solvent is water. The preferred concentration of the phosphine oxides used in the solutions depends on the particular phosphine oxide being used and on the degree of oil and water repellency desired, and may vary about from 3% to 10% by weight of the total solution. Aqueous solutions are preferred.

Polymerization of the phosphine oxides on the cellulosic material is carried out in the presence of latent acid catalysts such as magnesium chloride, zinc nitrate, or zinc fluoborate. The catalyst concentration may vary about from 0.5% to 2% by weight of the total solution, the preferred concentration depending on the concentration of the phosphine oxide.

The polymerization on cellulosic materials may be carried out by impregnating the cellulosic material with a solution of the phosphine oxide and catalyst, drying, and curing at temperatures ranging about from 120°C. to 160°C. for periods of time about from 3 minutes to 30 minutes, the longer times being used with the lower temperatures.

Cotton fabrics which have been treated by the processes of this invention are tested for oil repellency, water repellency, and dry cleaning durability by AATCC Standard Method No. 118-1966T, 22-1964, and 86-1963T, respectively. These tests are recommended by the American Association of Textile Chemists and Colorists. Laundering durability tests on the cotton fabrics are performed in an automatic home type washing machine using a detergent, followed by a 50 minute drying cycle in a tumble dryer. Screening laundry tests were carried out in a Tergitometer using a detergent.

The following examples illustrate procedures that have been successfully used in carrying out the invention and are not meant as a limitation thereof.

PREPARATION OF PERFLUOROALKYLPHOSPHONIC COMPOUNDS

EXAMPLE 1

Diethyl 1-iodo-1H,2H,2H-perfluorononylphosphonate (Ia) and tetraethyl 1-(1H,1H-perfluorooctyl)-3-iodo-1,3-trimethylenediphosphonate (Ib)

Diethylvinylphosphonate (57.8g., 0.35 mole) and perfluoroheptyl iodide (192.1 g, 0.39 mole) were placed into a 3-neck rb flask equipped with a magnetic stirrer, thermometer, gas inlet tube, and condenser connected to a mercury air trap. Light was excluded by covering the flask with aluminum foil. Azobis-(isobutyronitrile) catalyst (1.15 g, 0.007 mole) was added and the system flushed with nitrogen. The flask was heated in a water bath to 80° at which temperature an exothermic reaction began. An ice bath was used to keep the temperature below 150°. Reaction temperature was then maintained at approximately 85° for 6 hours. Unreacted material (95 g) was removed by vacuum distillation below 50° (0.3 mm). The residue (153.1 g) was crude mixed iodo-esters (I). A small amount of I was distilled under vacuu. The iodo-adduct (Ia) had bp 108°–114° (0.03 mm); $n^{20}D$ 1.3930. Anal. Calcd. for $C_{13}H_{13}F_{15}IO_3$ P: C, 23.65; H, 1.99; F, 43.17; I, 19.22; P, 4.69; mol. wt., 660. Found: C, 23.81; H, 2.02; F, 43.17; I, 19.09; P, 4.90; mol. wt. (benzene), 650.

The iodo-telomer (Ib) had bp 144°–6° (0.03 mm); $n^{20}D$ 1.4074. Anal. Calcd. for $C_{19}H_{26}F_{15}IO_6P_2$: C, 27.69; H, 3.18; F, 34.57; I, 15.40; P, 7.52; mol. wt., 824. Found: C, 27.80; H, 3.14; F, 34.55; I, 15.18; P, 7.24; mol. wt. (benzene), 830.

EXAMPLE 2

Diethyl 1H,1H,2H,2H-perfluorononylphosphonate (IIa) and tetraethyl 1-(1H,1H-perfluorooctyl)-1,3-trimethylenediphosphonate (IIb)

A slurry of 30 g of zinc dust in 200 ml of ethanol was heated in a water bath to 60° with stirring. An ethanolic solution of I (153.1 g) and 75 ml of conc. hydrochloric acid were added from separate dropping funnels within 30 minutes. The bath temperature was raised to 70° then 15 g of zinc and 40 ml of hydrochloric acid were added in increments over 1 hour. The mixture was heated an additional hour at 80°, cooled, filtered and concentrated on a rotary evaporator. The concentrate was washed with distilled water, then taken up in diethyl ether. The ether solution was washed with sodium bicarbonate, then with water to neutrality. The ether solution was dried over sodium sulfate, filtered and concentrated on a rotary evaporator. The reduced esters (113 g) were distilled under vacuum to give 40.9 g (22% yield from diethyl vinyl phosphonate (DEVP) of IIa, $n^{20}D$ 1.3538; 9.3 g of intermediate fraction, $n^{20}D$ 1.3694; 42.3 g (35% yield from DEVP) of IIb, $n^{20}D$ 1.3857; and 14.2 g of residue. The residue was stirred with absolute ethanol and filtered to give a fine brown solid (unidentified). The filtrate was concentrated to give a dark brown liquid believed to be another telomer, $n = 3$.

Redistillation of a portion of IIa gave bp 82°–84° (0.05 mm).

Anal. Calcd for $C_{13}H_{14}F_{15}O_3P$: C, 29.23; H, 2.64; F, 53.35; P, 5.80. Found: C, 29.34; H, 2.84; F, 53.18; P, 5.59.

IIb had bp 138°–140° (0.05 mm).

Anal. Calcd for $C_{19}H_{27}F_{15}O_6P_2$: C, 32.68; H, 3.90; F, 40.81; P, 8.87; mol. wt., 698. Found: C, 32.73; H, 4.00; F, 40.88; P, 8.69; mol. wt. (chloroform), 702.

Anal. Solid residue; C, 28.79; H, 3.36; F, 29.35; P, 10.34.

Anal. Liquid residue: Calcd for $C_{25}H_{40}F_{15}O_9P_3$: C, 34.82; H, 4.67; F, 33.04; P, 10.77. Found: C, 33.37; H, 4.33; F, 31.34; P, 9.79.

EXAMPLE 3

1H,1H,2H,2H-perfluorononylphosphonic dichloride (IIIa)

IIa (40 g, 0.075 mole) was heated with 100 ml of conc. hydrochloric acid at gentle reflux for 3 hours. The mixture was concentrated under vacuum to a gelatinous mass. Conc. hydrochloric acid (75 ml) was added to the mixture and refluxed overnight. The mixture was again concentrated under vacuum. Benzene was added and the remaining water removed by azeotropic distillation into a Dean-Stark trap. After removal of benzene, the solid residue was dried under vacuum at 105°C to a constant weight to give the crude acidadduct. This crude acid was dispersed in carbon tetrachloride and added to a rb flask equipped with a magnetic stirrer, condenser and drying tube. The mixture was heated to gentle reflux then phosphorus pentachloride (36.6 g, 0.176 mole) was added cautiously in small portions through the condenser. The addition was completed in 30 minutes, and the solution refluxed overnight. Sulfur dioxide was bubbled through the warm solution to remove excess phosphorus pentachloride. The solution was concentrated under water aspirator vacuum, and the residue distilled at 69°–72° (0.04 mm) to give an 83% yield (32.2 g, 0.062 mole) of IIIa, a white solid.

Anal. Calcd for $C_9H_4Cl_2F_{15}OP$: C, 20.99; H, 0.78; Cl, 13.77; F, 55.34; P, 6.01. Found: C, 20.79; H, 0.89; Cl, 13.76; F, 55.13; P, 5.99.

EXAMPLE 4

1-(1H,1H-perfluorooctyl)-1,3-trimethylenediphosphonic tetrachloride (IIIb)

IIb (57.8 g, 0.083 mole) was heated at gentle reflux for 6 hours with conc. hydrochloric acid (300 ml) in a 1 liter rb flask equipped with a 500 ml defoamer-bulb and a condenser. The mixture was cooled in the refrigerator and the liquid decanted from the solid. More hydrochloric acid was added and the procedure repeated. The gel-like material was concentrated in a large evaporating dish on the steam cone using benzene to remove residual water. The solid residue was dried under vacuum at 105°C to a constant weight to give the crude acid-telomer, which was then reacted with phosphorus pentachloride as described for the crude acid-adduct above. IIIb was distilled at 125°–6° (0.01 mm) to give a 40% yield (21.7 g, 0.033 mole) of a slightly yellow solid.

Anal. Calcd for $C_{11}H_7Cl_4F_{15}O_2P_2$: C, 20.02; H, 1.07; Cl, 21.49; F, 43.18; P, 9.39; mol. wt., 660. Found: C, 20.16; H, 1.14; Cl, 21.54; F, 43.29; P, 9.21; mol. wt. (chloroform), 673.

EXAMPLE 5

1H,1H,2H,2H-perfluorononylphosphonic acid (IVa)

IIIa (2 g, 0.004 mole) was dissolved in chloroform, then heated with 10 g of water in an evaporating dish. Residual water was removed by heating with benzene to dryness. The waxy solid residue was dried in a vacuum oven at 105° to a constant weight to give a 97% yield of IVa, mp 155°–158°.

Anal. Calcd for $C_9H_6F_{15}O_3P$: C, 22.61; H, 1.27; F, 59.61; P, 6.48; mol. wt., 478. Found: C, 22.33; H, 1.26; F, 59.73; P, 6.44; mol. wt. (methanol), 471.

EXAMPLE 6

1-(1H,1H-perfluorooctyl)-1,3-trimethylenediphosphonic acid (IVb)

IVb was prepared from IIIb as described for IVa except it was dried to constant weight in a vacuum desiccator at room temperature.

Anal. Calcd for $C_{11}H_{11}F_{15}O_6P_2$: C, 22.54, H, 1.89; F, 48.62; P, 10.57. Found: C, 22.75; H, 1.95; F, 48.68; P, 10.77.

EXAMPLE 7

1H,1H,2H,2H-perfluorononylbis(1-aziridinyl)phosphine oxide (Va)

Redistilled triethylamine (12.6 g, 0.124 mole) and redistilled aziridine (5.4 g, 0.124 mole) in carbon tetrachloride (100 ml) was added to a 4-neck rb flask equipped with a mechanical stirrer, thermometer, dropping funnel and condenser with drying tube. The flask was cooled to 5° in an ice bath. IIIa (29 g, 0.056 mole) in 75 ml of carbon tetrachloride was added from the dropping funnel at such a rate as to keep the reaction temperature below 10°. After the addition, the reaction temperature was allowed to rise to room temperature. The reaction mixture was heated at 35°–40° with stirring for 1 hour. The copious white precipitate was removed by vacuum filtration, rinsed thoroughly with carbon tetrachloride and dried to give 14.7 g (95% yield) of triethylamine hydrochloride. The filtrate was cooled at 0° overnight then filtered by gravity through sodium sulfate. The clear filtrate was concentrated to approximately 125 ml on a rotary evaporator below 40°. The solution was treated with decolorizing carbon and sodium sulfate then filtered by vacuum through distomaceous earth. The filtrate was again concentrated to approximately 75 ml then 150 ml of petroleum ether (30°–60°) was added. The solution was stored at −20° for 1 hour. The liquid was decanted through filter paper (filtrate No. 1). The slurry of white precipitate was redissolved in 100 ml of petroleum ether and stored at −20° overnight. The white waxy precipitate was filtered by vacuu, washed thoroughly with cold petroleum ether and dried in a desiccator to give 8.9 g of Va, mp 49°–50°; average aziridinyl assay of duplicate samples, 99.7%. The concentrated filtrate was diluted with petroleum ether and a second crop of crystals (10.1 g) was obtained; mp 42°–44°, average aziridinyl assay of duplicate samples, 97.7%. The filtrate was combined with filtrate No. 1 and concentrated to a yellow solid residue (7.1 g). The first and second crop of crystals gave a 64% yield of Va.

Anal. Calcd for $C_{13}H_{12}F_{15}N_2OP$: C, 29.59; H, 2.29; F, 53.95; N, 5.30; P, 5.86; mol. wt., 528. Found: C, 29.50; H, 2.41; F, 54.00; N, 5.33; P, 5.78; mol. wt. (methanol), 530.

EXAMPLE 8

1-(1H,1H-perfluorooctyl)-1,3-trimethylenebis[di(aziridinyl) phosphine oxide] (Vb)

Vb was prepared from IVb as described for Va to give a 64% yield; mp 103°–107°; aziridinyl assay 97.3%. (Vb was obtained as a slightly purer product when dissolved in carbon tetrachloride and a polymeric material removed by filtration; aziridinyl assay, 100.2%).

Anal. Calcd for $C_{19}H_{23}F_{15}N_4O_2P_2$: C, 33.25; H, 3.38; F, 41.52; N, 8.16; P, 9.03; mol. wt., 686. Found: C, 33.07; H, 3.14; F, 41.42; N, 8.08; P, 9.15; mol. wt. (chloroform), 691.

APPLICATION TO COTTON FABRIC

In all of the following examples cotton printcloth was used. In some cases the cloth contained the wash-wear finish, dimethylol ethylene urea. The printcloth was immersed in the solution and the excess squeezed out by passing through squeeze rolls to a wet pickup of 80–85%. The fabric was then dried and cured in a forced draft oven, and finally rinsed and dried.

The two compounds used in the following examples are 1H,1H,2H,2H-perfluorononylbis(1-aziridinyl)-phosphine oxide and 1-(1H,1H-perfluorooctyl)-1,3-trimethylene-bis[di(1-aziridinyl) phosphine oxide]. For brevity the two compounds will be designated "FNAPO" and telomer, respectively. The term oil rating will be abbreviated "OR."

EXAMPLE 9

A solution was prepared by dissolving FNAPO (0.5 grams) in a combination of water (4.5 grams) and ethanol (5.0 grams). The solution contained 5% FNAPO by weight. A sample of printcloth was immersed in 1% aqueous zinc fluoborate, the excess aqueezed out, and the fabric dried. The thus impregnated fabric was then impregnated with the FNAPO solution, dried for 30 minutes at room temperature and cured for 20 minutes at 120°C. The fabric had an oil rating (OR) of 5. the fabric had an OR of 2 after five laundering cycles and an OR of 5 after 3 hours extraction with tetrachloroethylene in a Soxhlet extractor.

EXAMPLE 10

Printcloth was treated as in Example 9 except that the solvent was ethanol instead of water-ethanol and the fabric was cured for 5 minutes at 150°C. The OR of the fabric was 6. After 5 launderings the OR was 2.

EXAMPLE 11

Printcloth was treated as in Example 9 except that the solvent was ethylene glycol monoethyl ether, and 2% zinc fluoborate was used, and the fabric was dried for 3 minutes at 80°C. The OR of the fabric was 6. After 5 launderings the OR was 3.

EXAMPLE 12

A 5% aqueous solution of FNAPO containing 1% zinc fluoborate was prepared and applied to cotton printcloth from a single bath. The cloth was dried for 5 minutes at 85°C and cured for 5 minutes at 140°C. The strength retention of the fabric was good. The weight gain of the fabric was 2.1% and the OR was 6. After 5 launderings the OR was 3 and after 5 drycleanings the OR was 2. The spray rating was 50 both before and after 5 launderings.

Printcloth was treated in the same manner except that a 3% aqueous solution of FNAPO containing 0.6% zinc fluoborate was used. Similar results on oil and water repellency and strength retention were obtained.

EXAMPLE 13

The two treatments in Example 12 were repeated except that the fabric used as treated with dimethylol ethyleneurea to impart wash-wear properties prior to treatment with FNAPO. Similar results on oil and water repellency were obtained. Fabric strength was lower due to the wash-wear finish.

EXAMPLE 14

Cotton printcloth was impregnated with an aqueous solution containing 5% FNAPO and 0.5% zinc fluoborate. The fabric was dried for 5 minutes at 85°C and cured for 5 minutes at 150°C. The OR was 6. After 5 launderings in a Tergitometer the OR was 2, and after a 3 hour extraction in a Soxhlet extractor the OR was 5.

EXAMPLE 15

Two printcloth samples were treated as in Example 14 except 1% zinc fluoborate was used and one sample was cured for 3 minutes at 160°C, and the other cured for 10 minutes at 160°C. The first sample had an OR of 5. After 5 launderings in a Tergitometer the Or was 3. The second sample had an original OR of 6, and an OR of 3 after 5 launderings in a Tergitometer. The OR of the samples was unaffected by extraction with tetrachloroethylene.

EXAMPLE 16

Cotton printcloth was impregnated with an aqueous solution containing 10% FNAPO and 1% zinc fluoborate. The fabric was dried for 5 minutes at 85°C and cured for 5 minutes at 160°C. The OR was 6 before and after extraction with tetrachloroethylene and 4 after five Tergitometer launderings.

EXAMPLE 17

Printcloth was treated as in Example 16 except a 5% solution of FNAPO was used and the fabric was cured for 30 minutes at 120°C without predrying. The OR was 6 before and after tetrachloroethylene extraction.

EXAMPLE 18

A 5% aqueous solution of telomer containing 1% zinc fluoborate was prepared and applied to cotton printcloth from a single bath. The cloth was dried for 5 minutes at 85°C and cured for 5 minutes at 140°C. The weight gain of the fabric was 3.5% and the OR was 2. After one home laundering the OR was zero, and after 4 drycleanings the OR was 1. The spray rating was 50 before and after 5 home launderings or 5 drycleanings. The OR was 2 after 3 hours extraction with tetrachloroethylene in a Soxhlet extractor.

We claim:
1. 1-(1H,1H-perfluorooctyl)-1,3-trimethylenediphosphonic acid.